United States Patent [19]

Donaldson

[11] 4,275,230
[45] Jun. 23, 1981

[54] PURIFICATION OF DICARBOXYLIC ACIDS

[75] Inventor: Peter A. Donaldson, Middlesbrough, England

[73] Assignee: Imperial Chemical Industries Limited, London, England

[21] Appl. No.: 969,431

[22] Filed: Dec. 14, 1978

Related U.S. Application Data

[63] Continuation of Ser. No. 816,667, Jul. 18, 1977, abandoned.

[30] Foreign Application Priority Data

Aug. 11, 1976 [GB] United Kingdom ............... 33383/76

[51] Int. Cl.³ ............................................. C07C 51/42

[52] U.S. Cl. .................................................... 562/486
[58] Field of Search ......................................... 562/486

[56] References Cited

U.S. PATENT DOCUMENTS

| 3,708,532 | 1/1973 | Ichikawa et al. ..................... 562/486 |
| 3,931,305 | 1/1976 | Fisher ................................. 562/486 |

Primary Examiner—Alan Siegel
Attorney, Agent, or Firm—Cushman, Darby & Cushman

[57] ABSTRACT

Crystallization of terephthalic acid from water at elevated temperature and pressure is effected in a continuous stage followed by a batch stage.

7 Claims, 1 Drawing Figure

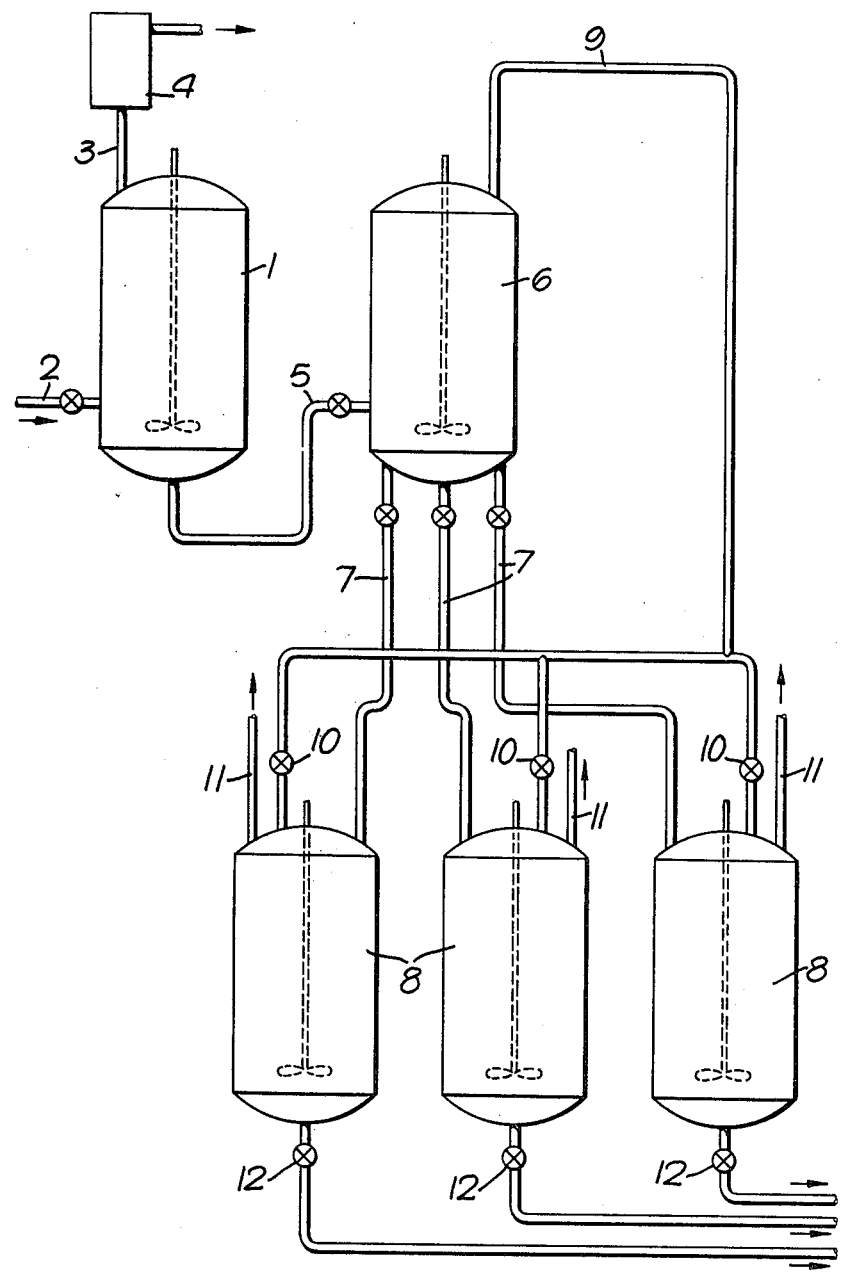

PURIFICATION OF DICARBOXYLIC ACIDS

This is a continuation of application Ser. No. 816,667, filed July 18, 1977, now abandoned.

DESCRIPTION OF THE INVENTION

This invention relates to the purification of dicarboxylic acids, more especially to the purification of terephthalic acid by crystallisation.

According to the invention a process for the cyrstallisation of terephthalic acid comprises:

(1) releasing continuously an aqueous solution of terephthalic acid at a temperature above 250° C. and under pressure to a continuous cyrstallisation stage operating at a lower pressure from which steam is released continuously to effect evaporative cooling whereby solid terephthalic acid crystallises to give an aqueous slurry thereof, (2) releasing the said slurry to a batch crystallisation stage comprising one or more batch crystallisers, each batch crystalliser being heated and pressurised to a temperature and pressure approaching that of the aqueous slurry effluent from the continuous crystallisation stage prior to receiving that slurry, and steam being released from each batch crystalliser after receiving slurry to effect evaporative cooling whereby further terephthalic acid crystallises, and (3) removing slurry from each batch crystalliser after releasing steam, and separating terephthalic acid from the mother liquor.

The batch crystallisers are preferably heated and pressurised by steam. An optional feature of our invention is to use steam released from the continuous crystallisation stage for this duty.

The aqueous solution of terephthalic acid at a temperature above 250° C. may be obtained by dissolving the acid in water above the specified temperature and at a pressure sufficient to keep the water substantially in the liquid phase. The pressure will normally be at least 40 bar absolute. Higher temperatures may be used, for example up to 350° C., and we prefer to use temperatures in the range 270° C. to 300° C. The concentration of the solution will normally be at least 10% by weight, is preferably from 15% to 30% and may be as high as 50% or more, although the concentration is limited by the solubility of the terephthalic acid at the lower temperatures.

Conveniently the aqueous solution fed to the continuous crystallisation stage is the effluent from a process is which terephthalic acid is purified from aldehyde-containing impurities, especially 4-carboxy-benzaldehyde, by catalytic hydrogenation in aqueous solution at elevated temperature and pressure. Such a process is described for example in British Patent Specification No. 994,769. In such a case the hydrogeanation catalyst will normally be separated, for example by filtration, from the aqueous solution prior to its being fed to the continuous crystallisation stage.

In the continuous crystallisation stage steam is released continuously as the aqueous solution is fed, to effect evaporative cooling of the solution resulting in crystallisation of a part of the terephthalic acid. The continuous crystallisation stage may be effected in a single crystalliser or in two or more crystallisers connected in series. The temperature in the continuous crystallisation stage is lower than that of the aqueous solution upstream of it and will normally be in the range 150° to 250° C., preferably 200° to 240° C. The pressure in the continuous crystallisation stage which is below that of the aqueous solution upstream of it, is adjusted to that required to attain the chosen temperature by evaporative cooling. Typical operating pressures are from 10 to 40 bar absolute. As a result of the crystallisation of terephthalic acid an aqueous slurry of the solid acid is obtained, typical slurry concentrations being from 15% to 30% by weight. Where more than one continuous crystalliser is used the temperatures and pressures in the successive crystallisers are progressively lower, and the slurry concentration progressively higher. We prefer to use one or two continuous crystallisers.

The aqueous slurry resulting from the continuous crystallisation stage is released to the batch crystallisation stage. Preferably there is a plurality of batch crystallisers, that is at least two and optionally more, for example up to 5 or more, to which the aqueous slurry is released in sequence. We prefer to use at least two batch crystallisers. The aqueous slurry effluent from the continuous crystallisation stage is fed to a batch crystalliser until that crystalliser has received the desired charge and, where more than one batch crystalliser is used, the feed is then switched to another batch crystalliser. The feed of slurry from the continuous crystallisation stage to one or other of the batch crystalliser may proceed without significant interruption. However, by suitable design of the crystalliser or crystallisers of the first crystallisation stage it can be arranged that changes of level can accommodate significant interruptions of feed to the batch crystallisers while the continuous feed of aqueous solution to the continuous crystallisation stage remains uninterrupted. Thus, feed of slurry from the continuous crystallisation stage to the batch crystallisers may occupy only a fraction, for example 10% to 30% of the time of any particular cycle.

Each batch crystalliser is heated and pressurised prior to receiving slurry from the continuous crystallisation stage preferably by steam and conveniently by the effluent steam from the continuous crystallisation stage. The aim is to bring the temperature of the batch crystalliser as near as possible to that of the slurry effluent from the continuous crystallisation stage. In practice the temperature in the pressurised batch crystalliser may be somewhat below that of the effluent slurry, for example up to 5° C. below, and the pressure will necessarily also be somewhat below that in the continuous crystallisation stage, typical pressures being from 10 to 40 bar absolute. When the batch crystalliser has reached the desired temperature and pressure it is charged with slurry from the continuous crystallisation stage. Steam is then released from the batch crystalliser to effect further evaporative cooling of the slurry, resulting in crystallisation of more terephthalic acid. Normally steam is released until the pressure in the batch crystalliser reaches that of the atmosphere and the temperature of the slurry is about 110° C., for example 100° to 120° C. The slurry is then removed from the batch crystalliser and solid terephthalic acid separated from the mother liquor by conventional means, for example by filtration or advantageously by centrifuging. However, it is possible to stop the release of steam when the pressure is still somewhat above that of the atmosphere, for example up to 5 bar absolute, and effect the separation of the solid terephthalic acid under pressure. The rate of release of steam from the crystallisers may be controlled so as to avoid loss of liquor from the vessel by frothing. The solid terephthalic acid may be subsequently dried in a suitable drying system.

The apparatus required for the process of our invention is conventional, the crystallisers consisting of any suitable pressure vessels with valved connections for receiving or discharging aqueous solution or slurry, or steam. The crystallisers are preferably agitated to maintain the slurry solids in proper suspension.

BRIEF DESCRIPTION OF THE DRAWING

The drawing schematically illustrates an apparatus for carrying out the process of the present invention.

DETAILED DESCRIPTION OF THE DRAWING

The process of our invention may be operated in the apparatus illustrated in the drawings in which a first continuous crystalliser 1 is fitted with an agitator, a valved connection 2 for receiving hot aqueous terephthalic acid solution, a connection 3 for releasing steam to a vent condenser 4, and a valved connection 5 for transferring slurry to an agitated second continuous crystalliser 6. The said crystalliser 6 is connected via valved connections 7 to each of three batch crystallisers 8 for transferring slurry thereto, and has a valved connection 9 to a steam main which is connected via valved branches 10 to each of the batch crystallisers 8. The batch crystallisers 8 are fitted with agitators, connections 11 to a waste steam system or to atmosphere, and valved connections 12 for discharging slurry to a system for separating solid terephthalic acid from mother liquor. In use, hot aqueous terephthalic acid under pressure (typically at 275° C. and 65 bar absolute) is fed continuously via connection 2 into the first continuous crystalliser 1 (operating typically at 235° C. and 30 bar absolute) and steam is released continuously via connection 3 to vent condenser 4 from which steam (typically at 17 bar absolute pressure) can be recovered. The aqueous terephthalic acid slurry formed by evaporative cooling (typically of 25% by weight slurry concentration) is transferred continuously via connection 5 to the second continuous crystalliser 6 (operating typically at 220° C. and 22 bar absolute) from which steam is released via connection 9 to a steam main and thence as required via one of the branches 10 to an empty batch crystalliser 8 to preheat it. Aqueous terephthalic acid slurry from the second continuous crystalliser 6 (typically of 27% by weight slurry concentration) is transferred intermittently via one of the connections 7 to an empty and preheated batch crystalliser 8. The operating cycle of each batch crystalliser is as follows:

(i) preheat and pressurise with steam from second continuous crystalliser 6, (ii) receive slurry from second continuous crystalliser 6, (iii) release steam resulting in further evaporative cooling and separation of terephthalic acid, and, (iv) discharge slurry via connection 12 to separation system.

The crystallisation of terephthalic acid from water at elevated temperature and pressure is already known and both batch and continuous processes for such an operation have been described. The process of our invention, which is neither wholly a batch process nor wholly a continuous process, offers technical advantages over these prior described processes. Thus in a wholly batch process, for example as described in British Patent Specification No. 1,152,575, the hot aqueous terephthalic acid os cooled in a single crystalliser by evaporative cooling by release of steam to the point at which the aqueous slurry is discharged to the separation system (although two or more crystallisers may be used in parallel with each other). The crystalliser has to be heated to the temperature and pressure of the hot aqueous solution prior to receiving it, but the steam released from the crystalliser is at too low a pressure for this purpose so high pressure steam has to be supplied to the system to preheat the crystalliser. In contrast, in our process, the steam released from the continuous crystallisation stage is at a suitable pressure for preheating the batch crystallisers, whereas the crystalliser or crystallisers of the continuous crystallisation stage require no preheating once it is in continuous operation. Moreover, more steam may be released from the continuous crystallisation stage than is required to preheat and pressurise the batch crystallisers and this steam is at a temperature and pressure high enough for further use. For example when two continuous crystallisers are used steam released from the second in series may be sufficient for preheating and pressurising the batch crystallisers, leaving the steam released from the first crystalliser for other use. If desired, the batch crystallisers may be preheated and pressurised using a separate source of steam and that released from the continuous crystallisation stage may be used wholly for other useful duty, but this does not affect the energy savings achieved by our process. In any event, the process of our invention results in energy savings compared with a wholly batch process, for example savings of from 1000 to 2500 MJ/tonne of terephthalic acid recrystallised.

On the other hand when terephthalic acid is crystallised wholly continuously, for example as described in British Patent Specification No. 1,152,575 where the aqueous slurry of terephthalic acid passes successively through each of three crystallisers arranged in series and operating at progressively lower temperatures, the degree of purification of the terephthalic acid achieved is lower than in the process of our invention. Crystallisation of terephthalic acid from water at elevated temperature and pressure has the principal aim of separating the water-soluble impurities. An important impurity of this kind is p-toluic acid which is formed as a by-product with terephthalic acid in the oxidation of p-xylene. p-Toluic acid is also formed by the catalytic hydrogenation of 4-carboxybenzaldehyde, another by-product in terephthalic acid produced by oxidation of suitable hydrocarbons, in the purification process by catalytic hydrogenation in aqueous solution at elevated temperature and pressure, the aqueous effluent from which may conveniently from the feed to the continuous crystallisation stage in the process of our invention. Thus the removal of by-product p-toluic acid is a very important part of the crystallisation process. By the process of our invention the p-toluic acid content of the terephthalic acid may typically be reduced to 50 to 100 parts per million (p.p.m.) whereas in a wholly continuously operated process, starting from a crude terephthalic acid of the same impurity level, the p-toluic acid content may be two to three times as great. In order to reduce the p-toluic acid content of terephthalic acid produced by a wholly continuously operated crystallisation process to an acceptable level, separation of the terephthalic acid from the mother liquor at a higher temperature and hence under pressure, for example as described in British Patent Specification No. 1,261,589, may be necessary. It is an advantage of our process that a suitably low p-toluic acid level may be achieved without the complication and additional capital and running costs of operating under pressure or the loss of yield which may accompany separation at a higher temperature. Correspondingly, a terephthalic acid of suitably low impurity level may be obtained by our process from a crude terephthalic acid of higher impurity level than could be used in a wholly continuous crystallisation process.

The process of our invention also has the advantage that it produces terephthalic acid which is of larger particle size than that produced by the wholly continuous process, and is more easily handeable and more readily slurried with ethylene glycol than that produced either in the wholly continuous or wholly batch processes. (Slurrying with ethylene glycol is a first step in the manufacture of polyethylene terephthalate from terephthalic acid). Again the process is more flexible in permitting the particle size of the terephthalic acid to be varied (by varying the conditions, especially the temperature, in the continuous and batch stages) than are either the wholly continuous or wholly batch processes.

EXAMPLE

Using apparatus as described above and illustrated in the drawings, but consisting of one continuous crystalliser and three batch crystallisers, terephthalic acid at a rate of 20 parts by weight per hour was fed as a 22% by weight aqueous solution at 275° C. and 68 bar (gauge) to the continuous crystalliser operating at 233° C. and 28 bar (gauge), steam being released continuously. The resulting aqueous slurry of terephthalic was released intermittently to each one of the batch crystallisers in turn at a rate of 14.7 parts by weight of terephthalic acid per batch, from which, when charged, steam was released until atmospheric pressure was reached, when the slurry was discharged and centrifuged, and the terephthalic acid dried. The batch crystallisers were heated to operating temperature (233° C.) before charging with slurry by steam, the amount of steam required for this duty being 0.272 parts by weight per part by weight of terephthalic acid crystallised. The total amount of steam released from the continuous crystalliser was 0.59 parts by weight per part by weight of terephthalic acid crystallised and that not used for preheating the batch crystallisers was capable of other useful duty. The isolated terephthalic acid had a p-toluic acid content of 65 p.p.m. The mean residence time of terephthalic acid in the continuous crystalliser was 19.6 minutes and the time of steam release in each of the batch crystallisers was 45 minutes.

When the same apparatus was used without release of steam from the continuous crystallisation vessel, that is when that vessel was used solely as a solution storage vessel, the process consumed steam at the rate of 0.591 parts by weight per part by weight of terephthalic acid crystallised. Compared with this process the process of our invention generated useable steam at the rate of $0.59 - 0.272 = 0.318$ parts by weight per part by weight of terephthalic acid crystallised. The net saving of energy in our process compared with the prior process is, therefore, 2300 MJ/tonne of terephthalic acid crystallised.

I claim:

1. A process for the crystallization of terephthalic acid which has been purified from 4-carboxybenzaldehyde by catalytic hydrogenation in aqueous solution at elevated temperature and pressure so as to convert the 4-carboxybenzaldehyde to p-toluic acid which comprises:
   (1) releasing continuously the aqueous solution consisting essentially of water, terephthalic acid and p-toluic acid at a temperature above 250° C. and under pressure to a continuous crystallization stage operating continuously to effect evaporative cooling whereby solid terephthalic acid crystallizes to give an aqueous slurry thereof,
   (2) releasing the said slurry to a batch crystallization stage comprising one or more batch crystallizers, each batch crystallizer being heated and pressurized to a temperature and pressure approaching that of the aqueous slurry effluent from the continuous crystallization stage prior to receiving that slurry and steam being released from each batch crystallizer after receiving slurry to effect evaporative cooling whereby further terephthalic acid crystallizers and
   (3) removing slurry from each batch crystallizer after releasing steam, and separating terephthalic acid from the aqueous mother liquor containing p-toluic acid.

2. The process of claim 1 in which the batch crystallisers are heated and pressurised by steam.

3. The process of claim 2 in which the steam used is that released from the continuous crystallisation stage.

4. The process of claim 1 in which the aqueous solution fed to the continuous crystallisation stage is at a temperature of 270° C. to 300° C.

5. The process of claim 1 in which the concentration of the aqueous solution fed to the continuous crystallisation stage is from 15% to 30% by weight.

6. The process of claim 1 in which the temperature in the continuous crystallisation stage is in the range 200° to 240° C.

7. The process of claim 1 in which steam is released from the batch crystallisers until atmospheric pressure is reached and the temperature of the slurry is from 100° to 120° C.

* * * * *